(12) United States Patent
Rong et al.

(10) Patent No.: US 11,783,483 B2
(45) Date of Patent: Oct. 10, 2023

(54) DETECTING ABNORMALITIES IN VITAL SIGNS OF SUBJECTS OF VIDEOS

(71) Applicants: Yu Rong, Phoenix, AZ (US); Daniel W. Bliss, Scottsdale, AZ (US)

(72) Inventors: Yu Rong, Phoenix, AZ (US); Daniel W. Bliss, Scottsdale, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 16/823,587

(22) Filed: Mar. 19, 2020

(65) Prior Publication Data
US 2020/0302609 A1    Sep. 24, 2020

Related U.S. Application Data

(60) Provisional application No. 62/820,559, filed on Mar. 19, 2019.

(51) Int. Cl.
*G06T 7/246*     (2017.01)
*G06V 40/40*     (2022.01)
(Continued)

(52) U.S. Cl.
CPC ............ *G06T 7/0016* (2013.01); *A61B 5/004* (2013.01); *A61B 5/0075* (2013.01);
(Continued)

(58) Field of Classification Search
CPC .................. G06T 7/0016; G06T 7/248; G06T 2207/10024; A61B 5/004; A61B 5/0075;
(Continued)

(56) References Cited

U.S. PATENT DOCUMENTS 8,483,761 B2    7/2013  Li et al.
9,164,167 B2   10/2015  Tyde et al.
(Continued)

FOREIGN PATENT DOCUMENTS

CN    106264501 A    1/2017
EP      3440991 A1    2/2019
(Continued)

OTHER PUBLICATIONS

Ming-Zher Poh, Daniel J. McDuff, and Rosalind W. Picard, "Non-contact, automated cardiac pulse measurements using video imaging and blind source separation." Optics express, vol. 18, Issue 10 (2010): 10762-74 (Year: 2010).*

(Continued)

*Primary Examiner* — Bernard Krasnic
(74) *Attorney, Agent, or Firm* — Withrow & Terranova, P.L.L.C.; Vincent K. Gustafson

(57) ABSTRACT

Detecting abnormalities in vital signs of subjects of videos is provided. Aspects of the present disclosure include methods, apparatuses, and systems to detect and measure vital sign information of one or more human subjects of a video and detect abnormalities in the vital sign information. In some examples, such abnormalities can be used to indicate video data is likely altered or fraudulent. In this regard, imaging photoplethysmography (IPPG) and advanced signal processing techniques, including adaptive color beamforming, can be used to extract the vital signs of the video subjects.

19 Claims, 7 Drawing Sheets

(51) Int. Cl.
*G06T 7/00* (2017.01)
*A61B 5/00* (2006.01)
*A61B 5/024* (2006.01)
*A61B 5/087* (2006.01)
*G06V 40/16* (2022.01)

(52) U.S. Cl.
CPC ........ *A61B 5/02416* (2013.01); *A61B 5/0873* (2013.01); *G06T 7/248* (2017.01); *G06V 40/16* (2022.01); *G06V 40/40* (2022.01); *G06T 2207/10024* (2013.01)

(58) Field of Classification Search
CPC .............. A61B 5/02416; A61B 5/0873; G06K 9/00221
See application file for complete search history.

(56) References Cited

U.S. PATENT DOCUMENTS

| | | | |
|---|---|---|---|
| 9,737,219 B2* | 8/2017 | Chen | A61B 5/024 |
| 9,971,027 B1 | 5/2018 | Stockmann et al. | |
| 10,753,727 B2 | 8/2020 | Klose et al. | |
| 10,918,287 B2 | 2/2021 | Islam | |
| 10,928,374 B2 | 2/2021 | Islam | |
| 2010/0152600 A1 | 6/2010 | Droitcour et al. | |
| 2012/0232388 A1* | 9/2012 | Curra | A61B 8/466 |
| | | | 600/438 |
| 2013/0030257 A1 | 1/2013 | Nakata et al. | |
| 2013/0300573 A1 | 11/2013 | Brown et al. | |
| 2013/0317377 A1 | 11/2013 | Gupta et al. | |
| 2014/0276089 A1* | 9/2014 | Kirenko | A61B 5/14551 |
| | | | 600/473 |
| 2014/0276099 A1 | 9/2014 | Kirenko et al. | |
| 2014/0276104 A1 | 9/2014 | Tao et al. | |
| 2014/0378809 A1 | 12/2014 | Weitnauer et al. | |
| 2015/0342535 A1 | 12/2015 | Chen | |
| 2015/0379370 A1* | 12/2015 | Clifton | A61B 5/0075 |
| | | | 382/128 |
| 2016/0188831 A1 | 6/2016 | Kurtz et al. | |
| 2016/0287208 A1* | 10/2016 | Zhai | A61B 5/0245 |
| 2016/0338604 A1 | 11/2016 | Wang et al. | |
| 2016/0343135 A1 | 11/2016 | De Haan et al. | |
| 2017/0042432 A1 | 2/2017 | Adib et al. | |
| 2017/0127988 A1 | 5/2017 | Tao et al. | |
| 2017/0174343 A1 | 6/2017 | Erickson et al. | |
| 2017/0341745 A1 | 11/2017 | Sekine et al. | |
| 2018/0049669 A1 | 2/2018 | Vu et al. | |
| 2018/0085009 A1 | 3/2018 | Aiello et al. | |
| 2018/0140255 A1 | 5/2018 | Tao et al. | |
| 2019/0050985 A1* | 2/2019 | Den Brinker | A61B 5/0295 |
| 2019/0057502 A1 | 2/2019 | Wang et al. | |
| 2019/0142289 A1 | 5/2019 | Bliss et al. | |
| 2019/0240535 A1 | 8/2019 | Santra et al. | |
| 2020/0271749 A1 | 8/2020 | Wu et al. | |
| 2020/0297227 A1 | 9/2020 | Rong et al. | |
| 2022/0142478 A1 | 5/2022 | Bliss et al. | |

FOREIGN PATENT DOCUMENTS

| | | | |
|---|---|---|---|
| EP | 3440996 A1 | 2/2019 | |
| JP | 2008532587 A * | 8/2008 | ............... A61B 5/00 |
| NO | 2020072297 A1 | 4/2020 | |
| WO | 2009009690 A2 | 1/2009 | |
| WO | 2013027027 A2 | 2/2013 | |
| WO | 2016185004 A1 | 11/2016 | |
| WO | 2017180985 A1 | 10/2017 | |
| WO | 2017195196 A1 | 11/2017 | |
| WO | 2019126476 A1 | 6/2019 | |
| WO | 2020191142 A1 | 9/2020 | |
| WO | 2021202677 A1 | 10/2021 | |

OTHER PUBLICATIONS

Sara Ashley O'Brien, "Deepfakes are coming. Is big Tech ready?" CNNMoney, Aug. 18, 2018 (Year: 2018).*
Christian Wiede, Julia Richter, André Apitzsch, Fajer KhairAldin, and Gangolf Hirtz. "Remote heart rate determination in RGB Data." In Proceedings of the 5th International Conference on Pattern Recognition Applications and Methods, pp. 240-246. 2016 (Year: 2016).*
Ewa Magdalena Nowara, Ashutosh Sabharwal, and Ashok Veeraraghavan. "Ppgsecure: Biometric presentation attack detection using photopletysmograms." In 2017 12th IEEE International Conference on Automatic Face & Gesture Recognition (FG 2017), pp. 56-62. IEEE, 2017 (Year: 2017).*
Shahana N Youseph, and Rajesh Roy Cherian. (2015). Pixel and Edge Based Illuminant Color Estimation for Image Forgery Detection. Procedia Computer Science. 46. 1635-1642. 10.1016/j.procs.2015.02.099 (Year: 2015).*
Yu, Y.P.—"Heart Rate Estimation From Facial Images Using Filter Bank"—ISCCSP 2014—pp. 69-72 (Year: 2014).*
Esteep, J.—"Recovering Pulse Rate During Motion Artifact with a Multi-Imager Array for Non-Contact Imaging Photoplethysmography"—IEEE 2014, pp. 1462-1469 (Year: 2014).*
Rahman, H.—"Real Time Heart Rate Monitoring From Facial RGB Color Video Using Webcam" SAIS 2016, pp. 1-8 (Year: 2016).*
Jensen, J.N.—"Camera-based Heart Rate Monitoring"—Kgs. Lyngby 2014, pp. 1-58 (Year: 2014).*
Unakafov, A.—"Pulse rate estimation using imaging photoplethysmography: generic framework and comparison of methods on a publicly available dataset"—Biomedical Physics & Engineering Express 2018, pp. 1-13 (Year: 2018).*
Non-Final Office Action for U.S. Appl. No. 16/190,687, dated Jan. 12, 2021, 14 pages.
Al-Naji, A. et al., "Remote Optical Cardiopulmonary Signal Extraction With Noise Artifact Removal, Multiple Subject Detection & Long-Distance," IEEE Access, vol. 6, 2018, IEEE, pp. 11573-11595.
Author Uknown, "Apple Watch Series 5," accessed Nov. 16, 2018 from https://www.apple.com/apple-watch-series-4/health/, 13 pages.
Author Uknown, "Shimmer3 ECG Unit," accessed Nov. 16, 2018 from http://www.shimmersensing.com/products/shimmer3-ecg-sensor, 6 pages.
Doerry, A., "Just Where Exactly is the Radar? (a.k.a. The Radar Antenna Phase Center)," Sandia Report SAND2013-10635, Dec. 2013, Sandia National Laboratories, 26 pages.
Fox, K. et al., "Resting Heart Rate in Cardiovascular Disease," Journal of the American College of Cardiology, vol. 50, No. 9, 2007, Elsevier Inc., pp. 823-830.
Guan, S. et al., "Automated DC Offset Calibration Strategy for Structural Health Monitoring Based on Portable CW Radar Sensor," IEEE Transactions on Instrumentation and Measurement, vol. 63, No. 12, Dec. 2014, IEEE, pp. 3111-3118.
Li, Changzhi, "Doppler Phase Modulation Effect for Non-contact Accurate Measurement of Vital Signs and other Periodic Movements—From Theory to CMOS System on Chip Integrations," A Dissertation presented to the Graduate School of the University of Florida, 2009, 129 pages.
Lin, J., "Noninvasive Microwave Measurement of Respiration," Proceedings of the IEEE, Oct. 1975, IEEE, p. 1530.
Rong, Y. et al., "Direct RF Signal Processing For Heart-Rate Monitoring Using UWB Impulse Radar," 2018 52nd Asilomar Conference on Signals, Systems, and Computers, Oct. 28-31, 2018, Pacific Grove, CA, IEEE, pp. 1215-1219.
Rong, Y. et al., "Remote Sensing for Vital Information Based on Spectral-Domain Harmonic Signatures," IEEE Transactions on Aerospace and Electronic Systems, vol. 55, No. 6, Dec. 2019, OAPA, pp. 3454-3465.
Singh, A. et al., "Data-Based Quadrature Imbalance Compensation for a CW Doppler Radar System," IEEE Transactions on Microwave Theory and Techniques, vol. 61, No. 4, Apr. 2013, IEEE, pp. 1718-1724.
Wang, S. et al., "A Novel Ultra-Wideband 80 GHz FMCW Radar System for Contactless Monitoring of Vital Signs," 2015 37th

(56) References Cited

OTHER PUBLICATIONS

Annual International Conference of the IEEE Engineering in Medicine and Biology Society (EMBC), Aug. 25-29, 2015, Milan, Italy, IEEE, pp. 4978-4981.

Wolff, C., "Organ-Pipe Scanner," accessed Feb. 2019 from https://www.radartutorial.eu/06.antennas/an66.en.html, 1 page.

International Search Report and Written Opinion for International Patent Application No. PCT/US2020/023533, dated Jun. 18, 2020, 11 pages.

Fathy, Ramzie, et al., "Comparison of UWB Doppler radar and Camera based Photoplethysmography in Non-contact Multiple Heartbeats Detection," BioWireleSS, 2016, IEEE, pp. 25-28.

Feng, Litong, et al., "Motion-Resistant Remote Imaging Photoplethysmography Based on the Optical Properties of Skin," IEEE Transactions on Circuits and Systems for Video Technology, vol. 25, Issue 5, May 2015, pp. 879-891.

Gauri, Zade, "A Modern Microwave Life Detection System for Human Being Buried Under Rubble," International Journal of Advanced Engineering Research and Studies, vol. 1, Issue 1, Oct. 2011, 9 pages.

Hussain, Malek, "Ultra-Wideband Impulse Radar-An Overview of thePrinciples," IEEE AES Systems Magazine, vol. 13, Issue 9, Sep. 1998, pp. 9-14.

Lazaro, A., et al., "Analysis of Vital Signs Monitoring Using an IR-UWB Radar," Progress In Electromagnetics Research, vol. 100, 2010, pp. 265-284.

Li, Changzhi, et al., "Complex Signal Demodulation and Random Body Movement Cancellation Techniques for Non-contact Vital Sign Detection,"Microwave Symposium Digest, 2008, IEEE, pp. 567-570.

Park, Byung-Kown, et al., "Arctangent Demodulation With DC Offset Compensation in Quadrature Doppler Radar Receiver Systems," IEEE Transactions on Microwave Theory and Techniques, vol. 55, Issue 5, May 2007, pp. 1073-1079.

Poh, Ming-Zher, et al., "Non-contact, automated cardiac pulse measurements using video imaging and blind source separation," Optics Express, vol. 18, Issue 10, May 2010, 13 pages.

Ren, Lingyun, et al., "Noncontact Heartbeat Detection using UWB Impulse Doppler Radar," BioWireleSS, 2015, IEEE,pp. 14-16.

Rong, Yu, et al., "Harmonics-Based Multiple Heartbeart Detection at Equal Distance using UWB Impulse Radar," IEEE Radar Conference, Apr. 2018, IEEE, pp. 1101-1105.

Singh, Megha, et al., "Reconstruction of Sequential Cardiac In-Plane Displacement Patterns on the Chest Wall by Laser Speckle Interferometry," IEEE Transactions on Biomedical Engineering, vol. 38, Issue 5, May 1991, pp. 483-489.

Wang, Jingyu, et al., "Noncontact Distance and Amplitude-Independent Vibration Measurement Based on an Extended DACM Algorithm," IEEE Transactions on Instrumentation and Measurement, vol. 63, Issue 1, Jan. 2014, pp. 145-153.

Yan, Jiaming, et al., "Through-Wall Multiple Targets Vital Signs Tracking Based on VMD Algorithm," Sensors, vol. 16, Issue 8, Aug. 2016, 11 pages.

Zade, G. et al., "A Modern Microwave Life Detection System for Human Being Buried Under Rubble", International Journal of Advanced Engineering Research and Studies, Oct. 2011, vol. 1, 9 pages.

Final Office Action for U.S. Appl. No. 16/190,687, dated May 12, 2021, 5 pages.

Advisory Action for U.S. Appl. No. 16/190,687, dated Jul. 26, 2021, 3 pages.

Notice of Allowance for U.S. Appl. No. 16/190,687, dated Aug. 31, 2021, 9 pages.

Notice of Allowance for U.S. Appl. No. 16/190,687, dated Dec. 24, 2021, 9 pages.

Ahmad, A. et al., "Vital signs monitoring of multiple people using a FMCW millimeter-wave sensor," 2018 IEEE Radar Conference (RadarConf18), Apr. 23-27, 2018, Oklahoma City, OK, USA, IEEE, 6 pages.

Alizadeh, M. et al., "Remote Monitoring of Human Vital Signs Using mm-Wave FMCW Radar," IEEE Access, vol. 7, Apr. 2019, IEEE, 12 pages.

Anderson, N. et al., "A 118-mW Pulse-Based Radar SoC in 55-nm CMOS for Non-Contact Human Vital Signs Detection," IEEE Journal of Solid-State Circuits, vol. 52, No. 12, Dec. 2017, IEEE, pp. 3421-3432.

Anderson, R. et al., "The Optics of Human Skin," Journal of Investigative Dermatology, vol. 77, Issue 1, Jul. 1981, Elsevier, pp. 13-19.

Allen, J., "Photoplethysmography and its application in clinical physiological measurement," Physiological Measurement, vol. 28, No. 3, Feb. 2007, IOP Publishing, 40 pages.

Biswas, D. et al., "Heart Rate Estimation From Wrist-Worn Photoplethysmography: A Review," IEEE Sensors Journal, vol. 19, Issue 16, Aug. 2019, IEEE, pp. 6560-6570.

Chen, K.-M. et al., "An X-Band Microwave Life-Detection System," IEEE Transactions on Biomedical Engineering, vol. BME-33, Issue 7, Jul. 1986, IEEE, 5 pages.

Chen, V.C. et al., "Micro-Doppler effect in radar: phenomenon, model, and simulation study," IEEE Transactions on Aerospace and Electronic Systems, vol. 42, Issue 1, Jan. 2006, IEEE, 20 pages.

Chen, K-M. et al., "Microwave life-detection systems for searching human subjects under earthquake rubble or behind barrier," IEEE Transactions on Biomedical Engineering, vol. 47, Issue 1, Jan. 2000, IEEE, pp. 105-114.

Chen, V. et al., "Time-Frequency Transforms for Radar Imaging and Signal Analysis," Artech House, 2002, 233 pages.

Churkin, S. et al., "Millimeter-wave radar for vital signs monitoring," 2015 IEEE International Conference on Microwaves, Communications, Antennas and Electronic Systems (COMCAS), Nov. 2-4, 2015, Tel Aviv, Israel, IEEE, 4 pages.

Damianou, D., "The wavelength dependence of the photoplethysmogram and its implication to pulse oximetry," Ph.D. Thesis, University of Nottingham, 1995, 223 pages.

Davila, M. et al., "The PhysioCam: Cardiac Pulse, Continuously Monitored by a Color Video Camera," Journal of Medical Devices, vol. 10, Issue 2, Jun. 2016, published online May 2016, 2 pages.

Fallow, B.A. et al., "Influence of skin type and wavelength on light wave reflectance," Journal of Clinical Monitoring and Computing, vol. 27, No. 3, Feb. 2013, 7 pages.

Feldman, Y. et al., "The electromagnetic response of human skin in the millimetre and submillimetre wave range," Physics in Medicine and Biology, vol. 54(11), Jul. 2009, 25 pages.

Fitzpatrick, T., "The validity and practicality of sun-reactive skin types I through VI," Archives of Dermatology, vol. 124, No. 6, Jun. 1988, pp. 869-871.

Gu, C. et al., "A Hybrid Radar-Camera Sensing System With Phase Compensation for Random Body Movement Cancellation in Doppler Vital Sign Detection," IEEE Transactions on Microwave Theory and Techniques, vol. 61, Issue 12, Dec. 2013, first published Nov. 2013, IEEE, 12 pages.

Hayut, I. et al., "The Helical Structure of Sweat Ducts: Their Influence on the Electromagnetic Reflection Spectrum of the Skin," IEEE Transactions on Terahertz Science and Technology, vol. 3, Issue 2, Mar. 2013, first published Dec. 2012, IEEE, 10 pages.

Holmes, G. et al., "Generating Rule Sets from Model Trees," 12th Australian Joint Conference on Artificial Intelligence, Dec. 1999, 9 pages.

Humphreys, K. et al., "Noncontact simultaneous dual wavelength photoplethysmography: a further step toward noncontact pulse oximetry," Review of Scientific Instruments, vol. 78, Issue 4, Apr. 2007, AIP Publishing, 7 pages.

Immoreev, I. et al., "UWB Radar for Patient Monitoring," IEEE Aerospace and Electronic Systems Magazine, vol. 23, Issue 11, Nov. 2008, IEEE, 8 pages.

IT'IS Foundation, "Overview—Database of Tissue Properties," 2010-2022, accessed Aug. 31, 2014 from https://itis.swiss/virtual-population/tissue-properties/database/database-summary/, 2 page.

Kamal, A. et al., "Skin photoplethysmography—a review," Computer Methods and Programs in Biomedicine, vol. 28, No. 4, Apr. 1989, pp. 257-269.

(56) References Cited

OTHER PUBLICATIONS

Kamshilin, A. et al., A new look at the essence of the imaging photoplethysmography, Scientific Reports, vol. 5:10494, , May 2015, 9 pages.

Kebe, M. et al., "Human Vital Signs Detection Methods and Potential Using Radars: A Review," Sensors, vol. 20, Mar. 2020, MDPI, 38 pages.

Klemm, M. et al., "Breast Cancer Detection using Symmetrical Antenna Array," The Second European Conference on Antennas and Propagation, EuCAP 2007, Nov. 11-16, 2007, Edinburgh, IET, 5 pages.

Laman, N. et al., "High-Resolution Waveguide THz Spectroscopy of Biological Molecules," Biophysical Journal, vol. 94, Issue 3, Feb. 2008, pp. 1010-1020.

Lazaro, A. et al., "Analysis of Vital Signs Monitoring Using an IR-UWB Radar," Progress In Electromagnetics Research, vol. 100, Jan. 2010, pp. 265-284.

Li, C. et al., "Experiment and Spectral Analysis of a Low-Power Ka-Band Heartbeat Detector Measuring From Four Sides of a Human Body," IEEE Transactions on Microwave Theory and Techniques, vol. 54, Issue 12, Dec. 2006, IEEE, 9 pages.

Li, C. et al., "Random Body Movement Cancellation in Doppler Radar Vital Sign Detection," IEEE Transactions on Microwave Theory and Techniques, vol. 56, Issue 12, Dec. 2008, first published Nov. 18, 2008, IEEE, 4 pages.

Noon, D.A., "Stepped-Frequency Radar Design and Signal Processing Enhances Ground Penetrating Radar Performance," A thesis submitted for the degree of Doctor of Philosophy (PhD) of The University of Queensland, Jan. 1996, 186 pages.

Nowara, E. et al., "SparsePPG: Towards Driver Monitoring Using Camera-Based Vital Signs Estimation in Near-Infrared," 2018 IEEE/CVF Conference on Computer Vision and Pattern Recognition Workshops (CVPRW), Jun. 18-22, 2018, Salt Lake City, UT, USA, IEEE, 10 pages.

Orfanidis, S. J, "Electromagnetic Waves and Antennas," 2002, Rutgers University, 547 pages.

Petkie, D. et al., "Remote respiration and heart rate monitoring with millimeter-wave/terahertz radars," Proceedings of SPIE, vol. 7117, Oct. 2008, 6 pages.

Petkie, D. et al., "Millimeter-Wave Radar for Vital Signs Sensing," Radar Sensor Technology XIII Conference, Apr. 13-15, 2009, Orlando, FL, 5 pages.

Poh, M.-Z. et al., "Advancements in Noncontact, Multiparameter Physiological Measurements Using a Webcam," IEEE Transactions on Biomedical Engineering, vol. 58, Issue 1, Jan. 2011, Oct. 14, 2010, IEEE, 5 pages.

Quinlan, R., "Learning with Continuous Classes," 5th Australian Joint Conference on Artifical Intelligence, Nov. 1992, 6 pages.

Reid, C. et al., "Terahertz Time-Domain Spectroscopy of Human Blood," IEEE Journal of Biomedical and Health Informatics, vol. 17, Issue 4, Jul. 2013, first published Apr. 2013, IEEE, 11 pages.

Ren, L. et al., "Phase-Based Methods for Heart Rate Detection Using UWB Impulse Doppler Radar," IEEE Transactions on Microwave Theory and Techniques, vol. 64, Issue 10, Oct. 2016, IEEE, 13 pages.

Rong, Y. et al., "Active Breathing Suppression for Improved Sleep Monitoring Heartbeat Detection Using UWB Radar," 2019 IEEE 8th International Workshop on Computational Advances in Multi-Sensor Adaptive Processing (CAMSAP), Dec. 15-18, 2019, IEEE, 5 pages.

Rong, Y. et al., "Cardiac Sensing Exploiting an Ultra-Wideband Terahertz Sensing System," 2020 IEEE International Radar Conference (RADAR), Apr. 28-30, 2020, Washington, DC, USA, IEEE, 5 pages.

Rong, Y. et al., "Harmonics-Based Multiple Heartbeat Detection at Equal Distance using UWB Impulse Radar," 2018 IEEE Radar Conference (RadarConf18), Apr. 23-27, 2018, Oklahoma City, OK, USA, IEEE, 5 pages.

Rong, Y. et al., "Is Radar Cardiography (RCG) Possible?," 2019 IEEE Radar Conference (RadarConf), Apr. 22-26, 2019, Boston, MA, USA, IEEE, 6 pages.

Rong, Y. et al., "Multiple source detection performance of linear sparse arrays," 2016 50th Asilomar Conference on Signals, Systems and Computers, Nov. 6-9, 2016, Pacific Grove, CA, USA, IEEE, 5 pages.

Rong, Y. et al., "Non-Contact Vital Signs Detection with UAV-Borne Radars," arXiv:2011.13982v1 [eess.SP], Nov. 27, 2020, 7 pages.

Rong, Y. et al., "Smart Homes: See Multiple Heartbeats Through Wall Using Wireless Signals," 2019 IEEE Radar Conference (RadarConf), Apr. 22-26, 2019, Boston, MA, USA, IEEE, 6 pages.

Spetlik, R. et al., "Non-Contact Reflectance Photoplethysmography: Progress, Limitations, and Myths," 2018 13th IEEE International Conference on Automatic Face & Gesture Recognition (FG 2018), May 15-19, 2018, IEEE, 8 pages.

Staderini, E.M., "UWB Radars in Medicine," IEEE Aerospace and Electronic Systems Magazine, vol. 17, No. 1, Feb. 2002, pp. 13-18.

Sun, Y. et al., "Noncontact imaging photoplethysmography to effectively access pulse rate variability," Journal of Biomedical Optics, vol. 18, No. 6, Jun. 2013, 10 pages.

Tang, M.-C. et al., "A Self- and Mutually Injection-Locked Radar System for Monitoring Vital Signs in Real Time With Random Body Movement Cancellation," IEEE Transactions on Microwave Theory and Techniques, vol. 64, Issue 12, Dec. 2016, first published Nov. 2016, IEEE, 11 pages.

Aoyagi, T. et al., "Pulse oximetry: Its invention, contribution to medicine, and future tasks," Anesthesia and Analgesia, vol. 94, Feb. 2002, 5 pages.

Benton, C. et al., "Terahertz Radar for Remote Measurement of Vital Signs," 2008 Joint Meeting of the APS Ohio-Region Section, the AAPT Southern Ohio Section, and the ACS Dayton-Section, Oct. 10-11, 2008, Dayton, Ohio, American Physical Society, Abstract only, 1 page.

Rong, Y. et al., "Respiration and Cardiac Activity Sensing Using 3-D Cameras," 2020 54th Asilomar Conference on Signals, Systems, and Computers, Nov. 1-4, 2020, Pacific Grove, CA, USA, IEEE, 5 pages.

Theofanopoulos, P.C. et al., "A Novel Fingerprint Scanning Method Using Terahertz Imaging," 2018 IEEE International Symposium on Antennas and Propagation & USNC/URSI National Radio Science Meeting, Jul. 8-13, 2018, Boston, MA, USA, IEEE, 2 pages.

Extended European Search Report for European Patent Application No. 20772680.3, dated Nov. 8, 2022, 8 pages.

Tang, M.-C. et al., "Single Self-Injection-Locked Radar With Two Antennas for Monitoring Vital Signs With Large Body Movement Cancellation," IEEE Transactions on Microwave Theory and Techniques, vol. 65, Issue 12, Dec. 2017, first published Nov. 2017, IEEE, 10 pages.

Theofanopoulos, P.C. et al., "A Terahertz Microscopy Technique for Sweat Duct Detection," 2018 IEEE/MTT-S International Microwave Symposium—IMS, Jun. 10-15, 2018, Philadelphia, PA, USA, IEEE, 4 pages.

Tripathi, S. et al., "Morphology of human sweat ducts observed by optical coherencetomography and their frequency of resonance in the terahertz frequency region," Scientific Reports, vol. 5, Article No. 9071, Mar. 2015, 7 pages.

Verkruysse, W. et al., "Remote plethysmographic imaging using ambient light," Optics Express, vol. 16, No. 26, Dec. 2008, 16 pages.

Wang, F.-K. et al., "Detection of Concealed Individuals Based on Their Vital Signs by Using a See-Through-Wall Imaging System With a Self-Injection-Locked Radar," IEEE Transactions on Microwave Theory and Techniques, vol. 61, Issue 1, Jan. 2013, Dec. 2012, IEEE, 9 pages.

Wang, W. et al., "Unsupervised Subject Detection via Remote-PPG," IEEE Transactions on Biomedical Engineering, vol. 62, No. 11, Nov. 2015, first published Jun. 2015, IEEE, 9 pages.

Wang, Y. et al., "Induction of model trees for predicting continuous classes," Proceedings of the poster papers of the 9th European Conference on Machine Learning, Apr. 1997, 12 pages.

(56) References Cited

OTHER PUBLICATIONS

Zhang, Q. et al., "Heart Rate Extraction Based on Near-Infrared Camera: Towards Driver State Monitoring," IEEE Access, vol. 6, Jun. 2018, IEEE, 11 pages.
Zhu et al., "Doppler Radar Techniques for Vital Signs Detection Featuring Noise Cancellations," 2019 IEEE MTT-S International Microwave Biomedical Conference, May 2019, IEEE, 6 pages.
Invitation to Pay Additional Fees for International Patent Application No. PCT/US2019/053425, dated Nov. 27, 2019, 2 pages.
International Search Report and Written Opinion for International Patent Application No. PCT/US2019/053425, dated Jan. 30, 2020, 10 pages.
International Preliminary Report on Patentability for International Patent Application No. PCT/US2019/053425, dated Apr. 15, 2021, 7 pages.
International Search Report and Written Opinion for International Patent Application No. PCT/US2021/025106, dated Jul. 20, 2021, 10 pages.
Al-Naji, A. et al., "Remote measurement of cardiopulmonary signal using an unmanned aerial vehicle," IOP Conference Series: Materials Science and Engineering, vol. 405, Sep. 2018, IOP Publishing, 10 pages.
Non-Final Office Action for U.S. Appl. No. 16/823,599, dated Feb. 1, 2023, 13 pages.
Notice of Allowance and Examiner-Initiated Interview Summary for U.S. Appl. No. 16/823,599, dated May 31, 2023, 10 pages.
Non-Final Office Action for U.S. Appl. No. 17/277,596, dated Aug. 18, 2023, 10 pages.

\* cited by examiner

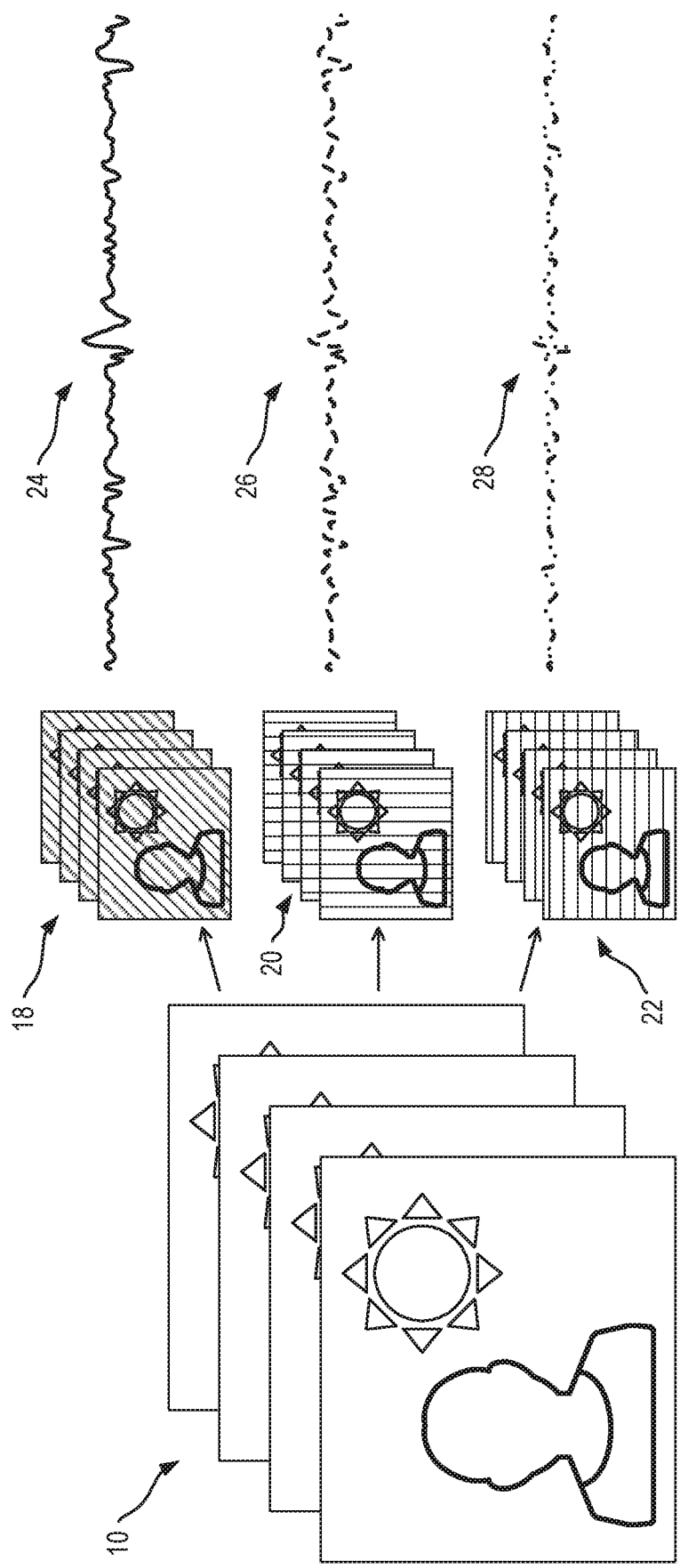

DETECTING ABNORMALITIES IN VITAL SIGNS OF SUBJECTS OF VIDEOS

RELATED APPLICATIONS

This application claims the benefit of provisional patent application Ser. No. 62/820,559, filed Mar. 19, 2019, the disclosure of which is hereby incorporated herein by reference in its entirety.

The present application is related to U.S. patent application Ser. No. 16/823,599, filed Mar. 19, 2020 (subsequently published as U.S. Patent Application Publication No. 2020/0297227 A1), entitled "VITAL SIGN MONITORING SYSTEM USING AN OPTICAL SENSOR," wherein each of the foregoing application and publication is hereby incorporated by reference hereiin in its entirety.

FIELD OF THE DISCLOSURE

This disclosure is related to vital sign detection in subjects of video data.

BACKGROUND

Due to recent advancements in digital video editing, it is becoming increasingly possible to create artificial videos which seem realistic both visually and audibly. For example, footage of influential persons, such as political leaders, thought leaders, and celebrities, can be spliced together to create fraudulent videos which can portray such influential persons as having said or done things which they did not. These are sometimes referred to as "deep fake" videos.

SUMMARY

Detecting abnormalities in vital signs of subjects of videos is provided. Aspects of the present disclosure include methods, apparatuses, and systems to detect and measure vital sign information of one or more human subjects of a video and detect abnormalities in the vital sign information. In some examples, such abnormalities can be used to indicate the video data is likely altered or fraudulent. In this regard, imaging photophlethysmography (IPPG) and advanced signal processing techniques, including adaptive color beamforming, can be used to extract the vital signs of the video subjects.

Embodiments described herein use IPPG to measure blood volume changes by detecting slight color variations in human skin in recorded video data. Spatially averaged skin-pixel values are tracked and measured, such as by using a face tracking algorithm in individual video frames. By adaptively combining a multi-color (e.g., red-green-blue (RGB)) time-series and concatenating resulting values, detected energy is maximized in a pulsatile direction to detect and measure vital sign(s) of interest. The vital sign information is then analyzed to detect abnormalities which may indicate the video data has been altered or is fraudulent.

An exemplary aspect relates to a method for detecting abnormalities in video data. The method includes receiving video data and extracting vital sign information of a subject from the video data using a region of interest on skin of the subject. The method further includes analyzing the vital sign information and determining whether an abnormality occurs in the analyzed vital sign information.

Another exemplary aspect relates to a fraud detector. The fraud detector includes a memory and a signal processor coupled to the memory. The signal processor is configured to obtain video data stored in the memory, extract vital sign information of a subject from the video data using a region of interest on skin of the subject, analyze the vital sign information to detect an abnormality, and if the abnormality is detected, determine the video data is fraudulent.

Another exemplary aspect relates to a method for detecting fraudulent video data. The method includes receiving video data, extracting vital sign information of a subject from the video data using a region of interest on skin of the subject, analyzing the vital sign information to detect an abnormality, and determining the video data is fraudulent based on the abnormality.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWING FIGURES

The accompanying drawing figures incorporated in and forming a part of this specification illustrate several aspects of the disclosure, and together with the description serve to explain the principles of the disclosure.

FIG. 2 is a schematic diagram of an exemplary approach to analyzing the video data of FIG. 1 using color beamforming to extract vital sign information.

DETAILED DESCRIPTION

Figure 1:
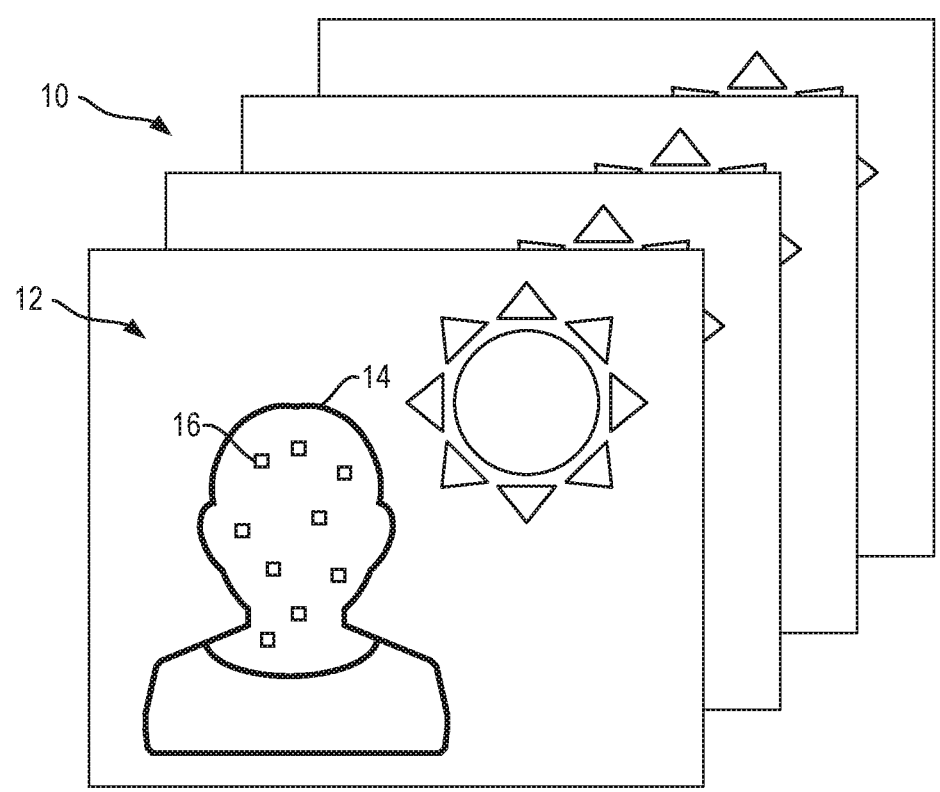
FIG. 1 is a graphical representation of exemplary video data comprising a sequence of captured frames including one or more subjects.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It will be understood that when an element such as a layer, region, or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. Likewise, it will be understood that when an element such as a layer, region, or substrate is referred to as being "over" or extending "over" another element, it can be directly over or extend directly over the other element or intervening elements may also be present. In contrast, when an element is referred to as being "directly over" or extending "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Relative terms such as "below" or "above" or "upper" or "lower" or "horizontal" or "vertical" may be used herein to describe a relationship of one element, layer, or region to another element, layer, or region as illustrated in the Figures. It will be understood that these terms and those discussed above are intended to encompass different orientations of the device in addition to the orientation depicted in the Figures.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Detecting abnormalities in vital signs of subjects of videos is provided. Aspects of the present disclosure include methods, apparatuses, and systems to detect and measure vital sign information of one or more human subjects of a video and detect abnormalities in the vital sign information. In some examples, such abnormalities can be used to indicate the video data is likely altered or fraudulent. In this regard, imaging photophlethysmography (IPPG) and advanced signal processing techniques, including adaptive color beamforming, can be used to extract the vital signs of the video subjects.

Embodiments described herein use IPPG to measure blood volume changes by detecting slight color variations in human skin in recorded video data. Spatially averaged skin-pixel values are tracked and measured, such as by using a face tracking algorithm in individual video frames. By adaptively combining a multi-color (e.g., red-green-blue (RGB)) time-series and concatenating resulting values, detected energy is maximized in a pulsatile direction to detect and measure vital sign(s) of interest. The vital sign information is then analyzed to detect abnormalities which may indicate the video data has been altered or is fraudulent.

FIG. 1 is a graphical representation of exemplary video data 10 comprising a sequence of captured frames 12 including one or more subjects 14. Embodiments described herein provide a solution for detecting abnormalities in the video data 10 which may indicate the video data 10 is altered from its original form or fraudulent. The abnormalities are detected through an analysis of vital sign information using an IPPG approach, using color beamforming and spectral analysis to extract the vital sign information. IPPG is an electro-optical technique for non-invasively measuring tissue blood volume pulses (BVPs) in the microvascular tissue bed underneath the skin of human subjects 14.

Embodiments described herein focus on a region of interest 16 (represented as a set of sample pixels) on a human face of the subject 14. The sequence of captured frames 12 can be recorded in a video format (e.g., a sequence of complete images or one or more reference images and difference vectors). The hemoglobin in blood can absorb light, therefore BVPs beneath the skin surface modulate light absorption by the skin during cardiac activity, appearing as slight color variations in the skin. These slight variations due to BVPs may be undetectable by human eyes, but signal processing techniques can be applied to the video data 10 to extract the BVPs and other vital signs (e.g., heart rate, heartbeat waveform, respiration rate) of the one or more subjects 14.

FIG. 2 is a schematic diagram of an exemplary approach to analyzing the video data 10 of FIG. 1 using color beamforming to extract vital sign information. A spatially averaged red-green-blue (RGB) time-series can be obtained to describe skin color changes over time by averaging skin-pixel values selected from a face tracking algorithm in individual video frames and concatenating the resulting values from each color channel 18, 20, 22. For example, a red color channel 18 of the region of interest 16 can be spatially averaged and represented by a red time-series 24. Similarly, a green color channel 20 can be represented by a green time-series 26, and a blue color channel 22 can be represented by a blue time-series 28. Adaptive color beamforming is used to adaptively combine the RGB color time-series (combining the red time-series 24, the green time-series 26, and the blue time-series 28) and maximize the energy in the pulsatile direction.

Figure 3A:
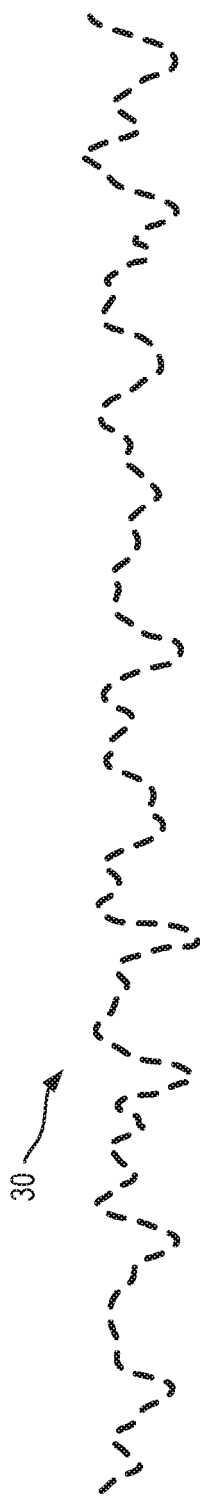
FIG. 3A is a graphical representation of a traditional fixed color combining approach to photophlethysmography.

FIG. 3A is a graphical representation of a traditional fixed color combining approach to photophlethysmography. Under the traditional approach, only the red and green color channels are combined at a fixed ratio, such as by weighting the red time-series 24 of FIG. 2 at −0.71 and the green time-series 26 at 0.71 (while ignoring the blue time-series 28). This produces a red-green time-series 30.

Figure 3B:
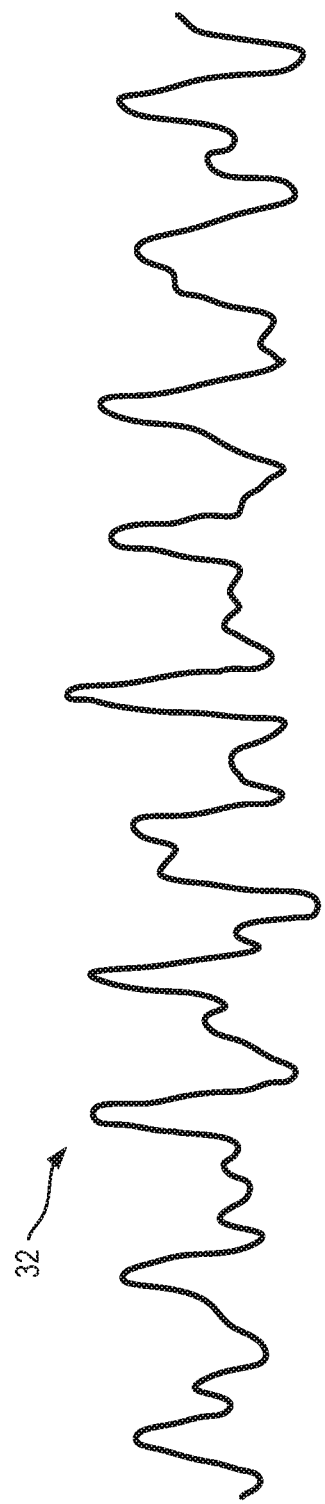
FIG. 3B is a graphical representation of results of the approach to analyzing the video data of FIG. 2.

FIG. 3B is a graphical representation of results of the approach to analyzing the video data 10 of FIG. 2. Embodiments described herein apply adaptive color beamforming to adaptively combine the red time-series 24, the green time-series 26, and the blue time-series 28 of FIG. 2 into an RGB color time-series 32. The beamforming weights can be appropriately selected based on the spectral energy distribution of the RGB time-series 32 within the frequency range of a human heart rate. This exploits the facts that (1) the pulsatile motion in different color channels has the same frequency in the spectral domain, and (2) motions or changes in the background (e.g., illumination) vary across different spectral components.

An exemplary RGB color beamforming algorithm can be implemented as follows. The spatially averaged RGB color time-series are processed blockwise:

$$[R_j^i; G_j^i; B_j^i] = \left[\frac{\Sigma_{ROI,k}\text{pixel}_k^{red}}{|ROI|}; \frac{\Sigma_{ROI,k}\text{pixel}_k^{green}}{|ROI|}; \frac{\Sigma_{ROI,k}\text{pixel}_k^{blue}}{|ROI|}\right] \quad \text{Equation 1}$$

where $R_j^i$ denotes the sample value at an i-th processing interval at a j-th index. At every processing time, a total number of N samples is obtained, $j=1, \ldots, N$. |ROI| denotes the number of image pixels in the region of interest.

Two covariances are constructed based on the possible human heart rate frequency range. The spectral components within this region are used to construct a spectral covariance matrix that most likely contains the pulsatile information. The spectral components outside this region are treated as background noise and random motion not of interest, and thus can be used to build a noise-related covariance matrix. For a normal resting heart rate, the frequency is from about 50 to 100 beats per minute. The spatially averaged RGB color time-series are filtered at this frequency region:

$$[R_{hr}^i; G_{hr}^i; B_{hr}^i] = \text{filter}\{|R^i; G^i; B^i|\} \quad \text{Equation 2}$$

where $B^i$ is a 1 by N vector. The pulse related RGB covariance is given as:

$$COV_{hr}^i = \frac{1}{N}[R_{hr}^i; G_{hr}^i; B_{hr}^i][R_{hr}^i; G_{hr}^i; B_{hr}^i]^T \quad \text{Equation 3}$$

where T denotes matrix transpose.

For convenience, the entire RGB color time-series are used to construct the background covariance matrix since the heartbeat activity is limited in a small fraction of the entire spectrum. Similarly, the noise related covariance matrix is given as:

$$COV_{noi}^i = \frac{1}{N}[R^i; G^i; B^i][R^i; G^i; B^i]^T \quad \text{Equation 4}$$

In order to emphasize the pulsatile related spectral energy in the covariance matrix, a noise-suppressed pulsatile spectral covariance is obtained by multiplying the matrix inversion of the noise-related covariance matrix to the spectral covariance matrix:

$$COV_{sup}^i = \{COV_{noi}^i\}^{-1} COV_{hr}^i \quad \text{Equation 5}$$

Optimal beamforming weights are directly related to the direction represented by an eigenvector associated with the maximum eigenvalues of the noise-suppressed pulsatile spectral covariance matrix:

$$[Vec, Val] = eig\{COV_{sup}^i\} \quad \text{Equation 6}$$

where eig denotes the eigenvalue decomposition operation, and Vec and Val represent the eigenvector matrix and the associated eigenvalues. If both are sorted in descending order, the optimal color beamforming weight, a 3 by 1 vector, maximizing the pulse energy while suppressing the background noise is given as:

$$w_{hr}^{opt} = Vec(:,1) \quad \text{Equation 7}$$

By applying the RGB color beamforming weights to the RGB color time-series, the desired pulsatile variation $p^i$ is obtained:

$$p^i = \{w_{hr}^{opt}\}^T [R^i; G^i; B^i] \quad \text{Equation 8}$$

This results in the RGB time-series 32, such as the example illustrated in FIG. 3B. Thus, the color beamforming approach outperforms the color difference algorithm of FIG. 3A.

Figure 4:
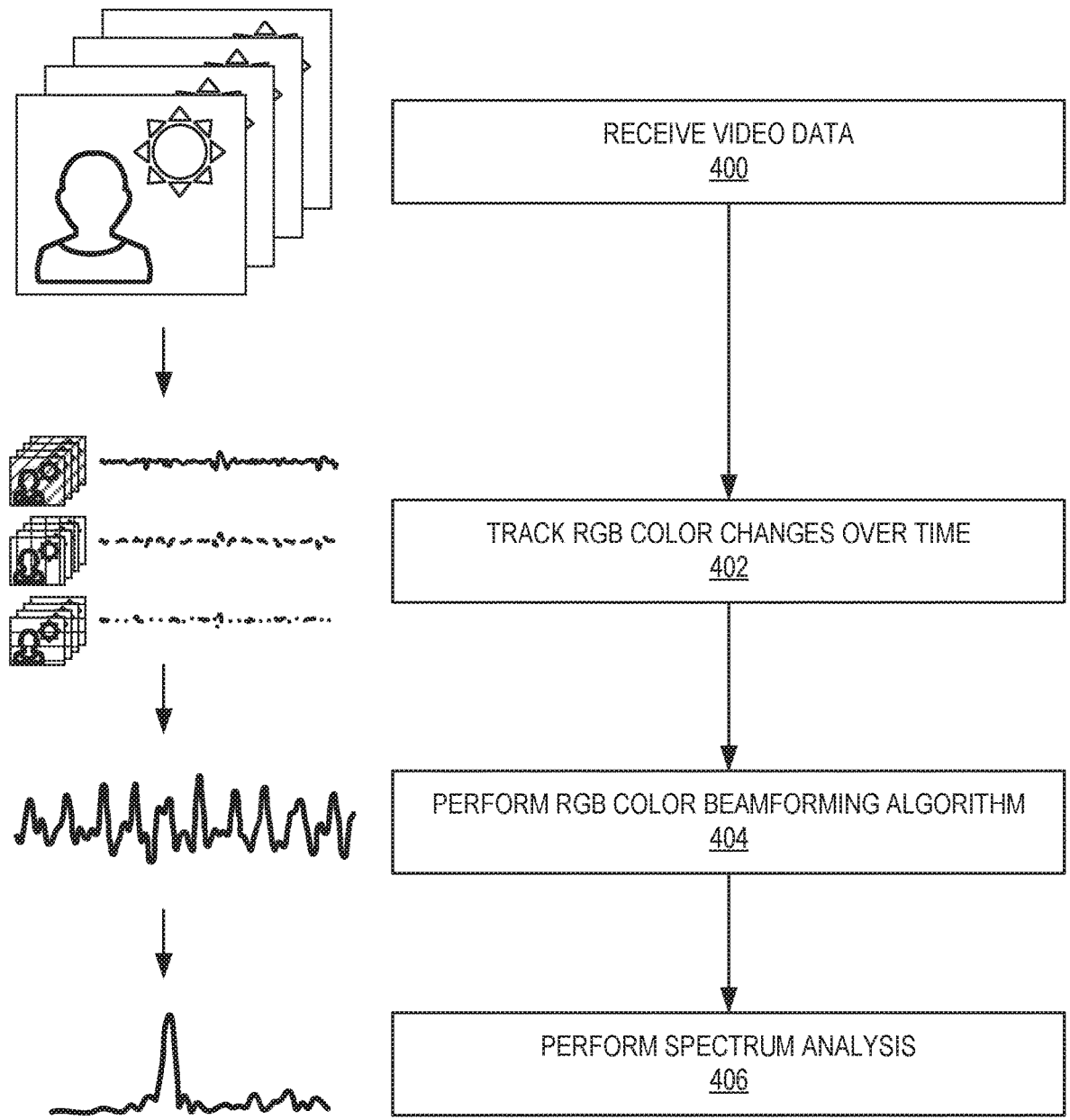
FIG. 4 is a schematic diagram of an exemplary imaging photophlethysmography (IPPG) approach described herein using color beamforming and spectral analysis to extract vital signs of a subject.

FIG. 4 is a schematic diagram of an exemplary IPPG approach described herein using color beamforming and spectral analysis to extract vital signs of a subject. With reference to FIGS. 2-4, the IPPG approach can begin with receiving video data (e.g., from a memory) and focusing on the region of interest 16 on the human face of the subject 14 (block 400). Changes in the sequence of captured frames 12 are recorded and tracked over time (e.g., using the face tracking algorithm) and spatially averaged to produce the red time-series 24, the green time-series 26, and the blue time-series 28 (block 402).

The RGB beamforming algorithm described above is used to adaptively combine the red time-series 24, the green time-series 26, and the blue time-series 28 into the RGB color time-series 32 (block 404). The beamforming weights can be appropriately selected based on the spectral energy distribution of the RGB time-series 32 within the frequency range of a human heart rate (block 406). In this regard, the spectral components within the region of interest 16 are used to construct the spectral covariance matrix that most likely contains the pulsatile information, where spectral components outside this region are treated as background noise to build a noise-related covariance matrix to further improve the extracted heart rate and/or heartbeat waveform.

The same concept described with regard to FIGS. 2-4 above can be applied for respiration detection. There are two differences here: 1) the region of interest in the recorded images are different and 2) the spectral frequency range of interest is different. In order to obtain maximum respiration sensitivity, the region of interest is selected as a relevant body part, such as a subject's neck and/or front chest. In order to construct the respiratory related covariance matrix, the spatially averaged RGB color time-series at the respiration region of interest are filtered at a frequency region ranging from 10 to 30 breaths per minute. Then the remaining steps follow the approach described above.

Figure 5:
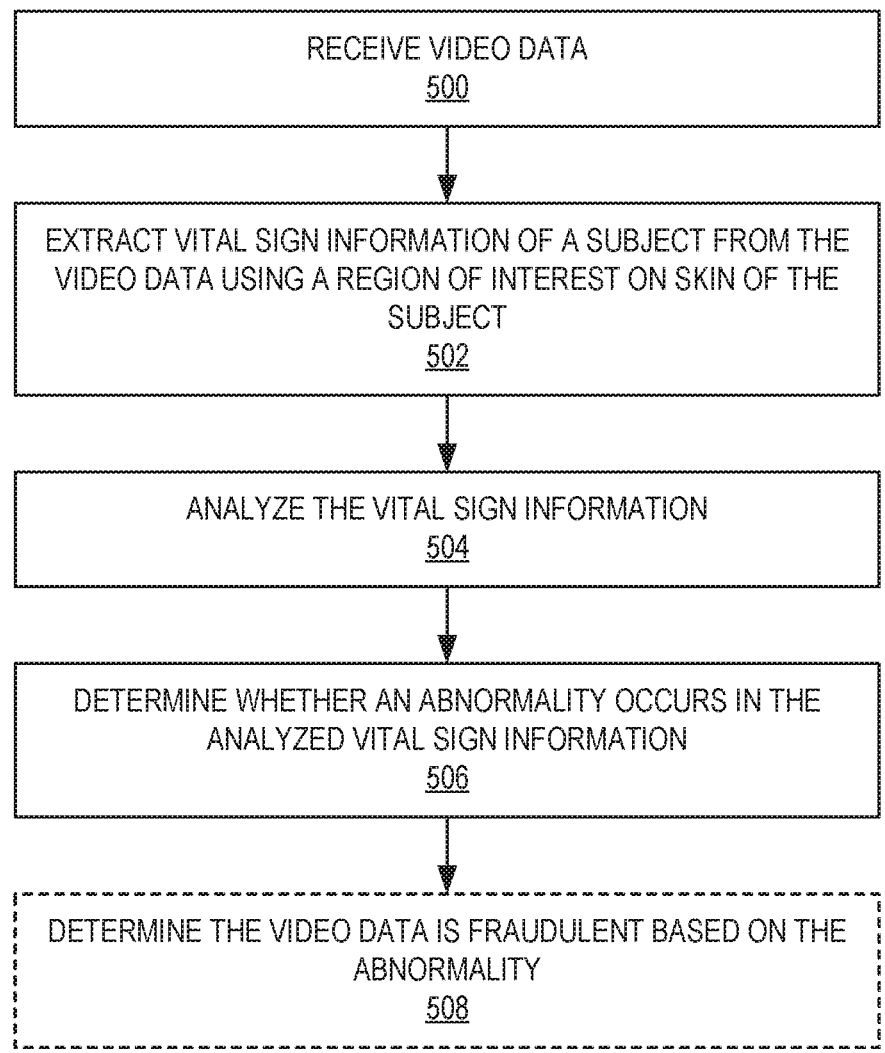
FIG. 5 is a schematic block diagram of an exemplary method for detecting abnormalities in video data according to embodiments described herein.

FIG. 5 is a schematic block diagram of an exemplary method for detecting abnormalities in video data according to embodiments described herein. The method begins with receiving video data (block 500). The method further includes extracting vital sign information of a subject from the video data using a region of interest on skin of the subject (block 502). The method further includes analyzing the vital sign information (block 504). The method further includes determining whether an abnormality occurs in the analyzed vital sign information (block 506). The method may optionally include determining the video data is fraudulent based on the abnormality (block 508).

Figure 6:
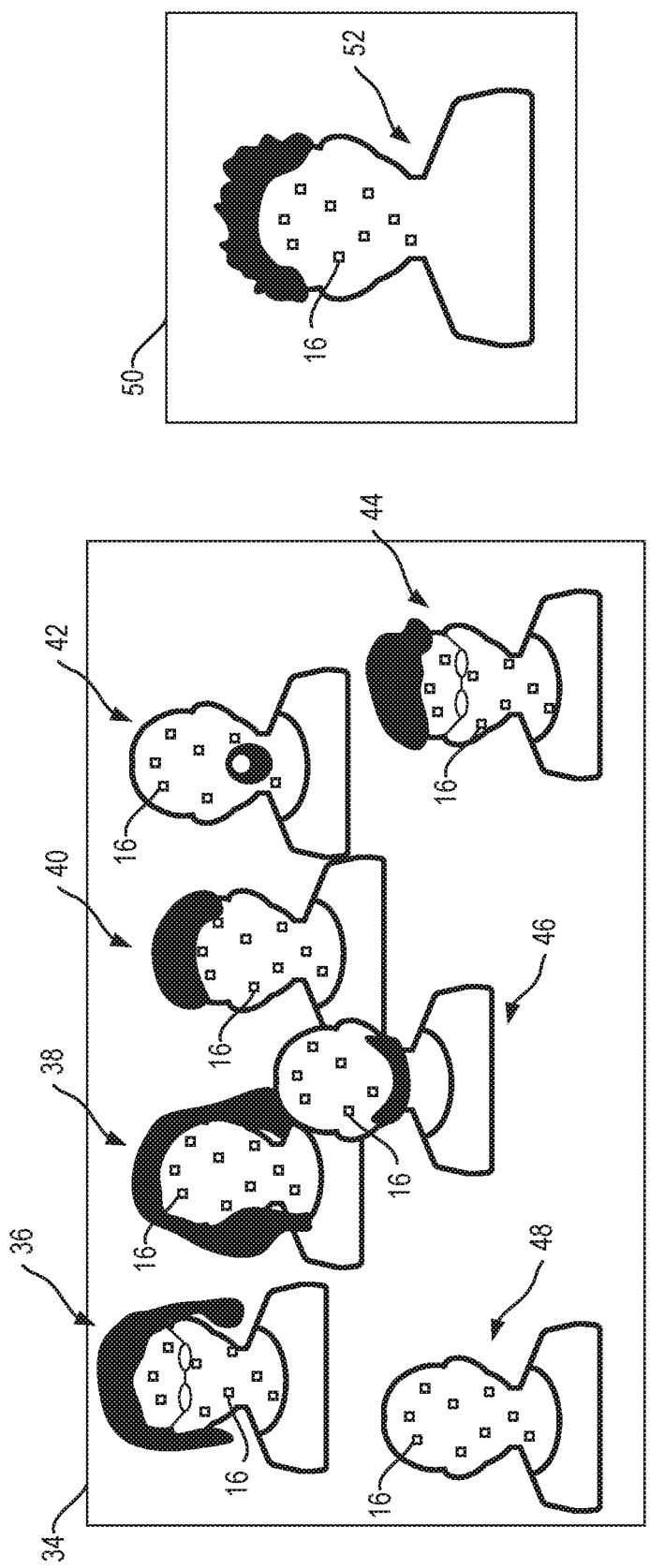
FIG. 6 is a graphical representation comparing a first video frame having multiple subjects with vital signs within normal ranges and a second video frame of a subject with an abnormal vital sign.

FIG. 6 is a graphical representation comparing a first video 34 having multiple subjects 36, 38, 40, 42, 44, 46, 48 with vital signs within normal ranges and a second video 50 of a subject 52 with an abnormal vital sign. As described above, exemplary aspects of this disclosure extract and analyze heart rate and other vital signs (e.g., respiration rate) from video data, such as the first video 34 and the second video 50, to provide a complete systematic solution for detecting fraudulent video content, especially in a complex video scene. By extracting and analyzing vital sign information, fake human subjects or fraudulent human faces can be identified from a group of subjects inside the video data. Embodiments use information entropy to quantitatively measure the probability of fraudulent content in the video data based on extracted temporal structure of the vital signs, such as heartbeat waveform and respiration pattern.

In this regard, a multiple-face detection algorithm is applied to each of the first video 34 and the second video 50 in order to inspect their respective video content. Then the facial region of interest 16 of each potential subject 36, 38, 40, 42, 44, 46, 48, 52 is determined. A tracking algorithm can adjust for motion (e.g., head motion) and provide accurate facial regions of interest 16 over time.

Next, the fraud detector spatially averages the facial pixels within each region of interest 16 to form RGB time-series (red, green, and blue channels) by concatenating each video frame in the respective first video 34 and second video 50. In order to form the final temporal series related to heartbeat, the pulse extraction approach using color beamforming described above with respect to FIGS. 2-4 can be applied.

Based on the extracted pulse variation, the heartbeat rhythm is analyzed and checked for the occurrence of abnormal patterns (e.g., constant heart rate or large variations in beat to beat intervals). If these events occur, it can be deemed more likely that the video data under inspection contains artificial edits.

For example, analysis of the first video 34 does not indicate abnormal vital sign activity in any of the subjects—a first subject 36 has a heart rate of 91 beats per minute (bpm) (normal adult human heart rates are generally between 50 and 100 bpm), a second subject 38 has a heart rate of 53 bpm, a third subject 40 has a heart rate of 60 bpm, a fourth subject 42 has a heart rate of 58 bpm, a fifth subject 44 has a heart rate of 55 bpm, a sixth subject 46 has a heart rate of 63 bpm, and a seventh subject 48 has a heart rate of 68 bpm. No abnormal patterns are detected in these subjects and therefore the fraud detector may not determine the first video 34 is fraudulent based on this analysis.

However, analysis of the second video 50 indicates abnormal vital sign activity in its subject—this subject 52 has a heart rate of 300 bpm, well outside the normal human range for heart rate. In some embodiments, the second video 50 may be determined to be fraudulent based on this analysis. Further examples may additionally or alternatively analyze respiratory activity or other vital signs in a similar manner.

In some embodiments, this vital sign analysis may be sufficient, standing alone, to determine a video is fraudulent. In other embodiments, the vital sign analysis may be only a part of the fraud detector's analysis. For example, background color changes (e.g., rapid color changes or overly static colors), dynamic edge detection (e.g., to find inconsistent or unexpected edge motion), and other video artifacts may be used in an entropy analysis to determine a likelihood a video is fraudulent.

Figure 7:
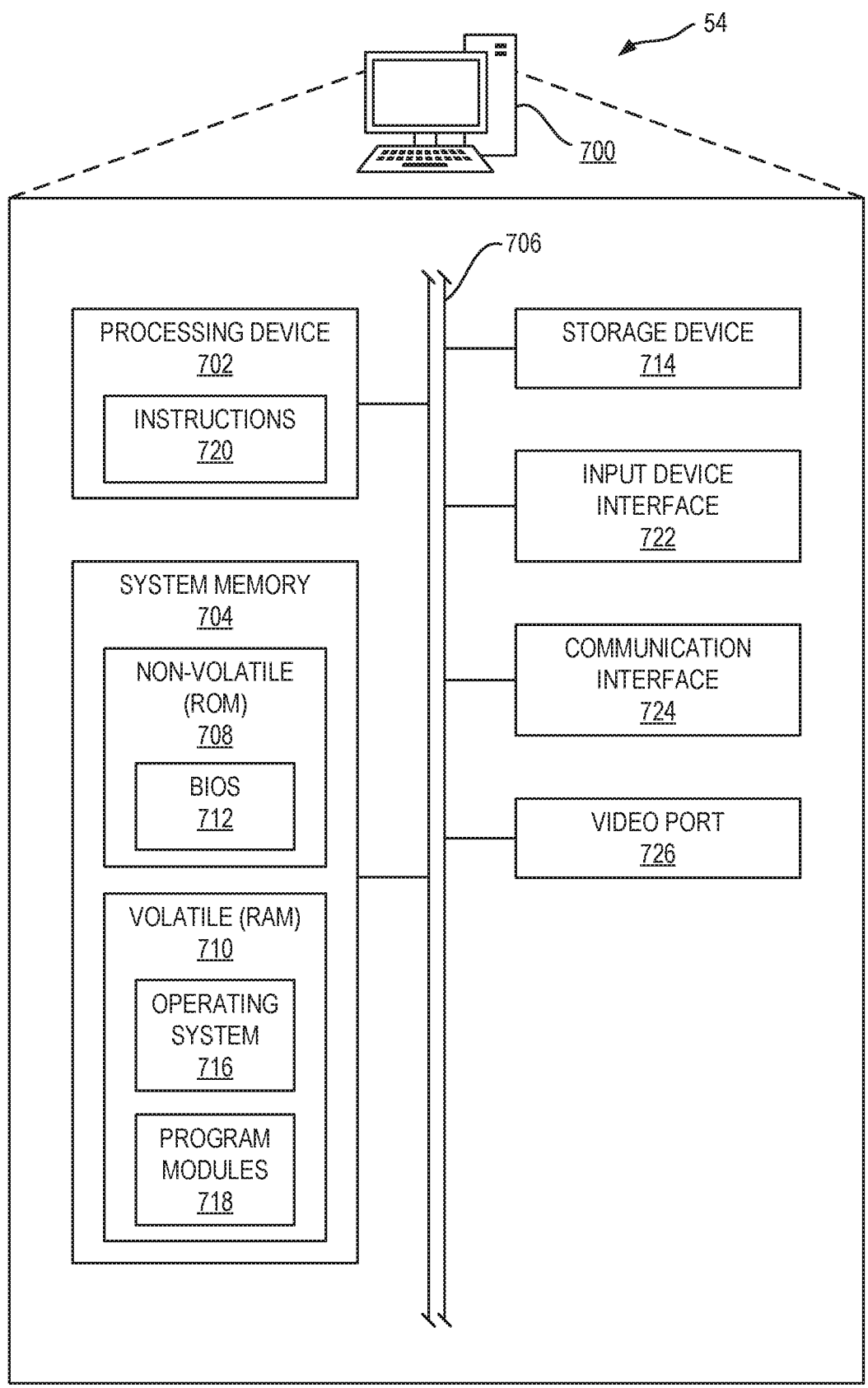
FIG. 7 is a block diagram of a fraud detector suitable for detecting fraudulent video data according to embodiments disclosed herein.

FIG. 7 is a block diagram of a fraud detector 54 suitable for detecting fraudulent video data according to embodiments disclosed herein. The fraud detector 54 includes or is implemented as a computer system 700, which comprises any computing or electronic device capable of including firmware, hardware, and/or executing software instructions that could be used to perform any of the methods or functions described above. In this regard, the computer system 700 may be a circuit or circuits included in an electronic board card, such as a printed circuit board (PCB), a server, a personal computer, a desktop computer, a laptop computer, an array of computers, a personal digital assistant (PDA), a computing pad, a mobile device, or any other device, and may represent, for example, a server or a user's computer.

The exemplary computer system 700 in this embodiment includes a processing device 702 or processor, a system memory 704, and a system bus 706. The system memory 704 may include non-volatile memory 708 and volatile memory 710. The non-volatile memory 708 may include read-only memory (ROM), erasable programmable read-only memory (EPROM), electrically erasable programmable read-only memory (EEPROM), and the like. The volatile memory 710 generally includes random-access memory (RAM) (e.g., dynamic random-access memory (DRAM), such as synchronous DRAM (SDRAM)). A basic input/output system (BIOS) 712 may be stored in the non-volatile memory 708 and can include the basic routines that help to transfer information between elements within the computer system 700.

The system bus 706 provides an interface for system components including, but not limited to, the system memory 704 and the processing device 702. The system bus 706 may be any of several types of bus structures that may further interconnect to a memory bus (with or without a memory controller), a peripheral bus, and/or a local bus using any of a variety of commercially available bus architectures.

The processing device 702 represents one or more commercially available or proprietary general-purpose processing devices, such as a microprocessor, central processing unit (CPU), or the like. More particularly, the processing device 702 may be a complex instruction set computing (CISC) microprocessor, a reduced instruction set computing (RISC) microprocessor, a very long instruction word (VLIW) microprocessor, a processor implementing other instruction sets, or other processors implementing a combination of instruction sets. The processing device 702 is configured to execute processing logic instructions for performing the operations and steps discussed herein.

In this regard, the various illustrative logical blocks, modules, and circuits described in connection with the embodiments disclosed herein may be implemented or performed with the processing device 702, which may be a microprocessor, field programmable gate array (FPGA), a digital signal processor (DSP), an application-specific integrated circuit (ASIC), or other programmable logic device, a discrete gate or transistor logic, discrete hardware components, or any combination thereof designed to perform the functions described herein. Furthermore, the processing device 702 may be a microprocessor, or may be any conventional processor, controller, microcontroller, or state machine. The processing device 702 may also be implemented as a combination of computing devices (e.g., a combination of a DSP and a microprocessor, a plurality of microprocessors, one or more microprocessors in conjunction with a DSP core, or any other such configuration).

The computer system 700 may further include or be coupled to a non-transitory computer-readable storage medium, such as a storage device 714, which may represent an internal or external hard disk drive (HDD), flash memory, or the like. The storage device 714 and other drives associated with computer-readable media and computer-usable media may provide non-volatile storage of data, data structures, computer-executable instructions, and the like. Although the description of computer-readable media above refers to an HDD, it should be appreciated that other types of media that are readable by a computer, such as optical disks, magnetic cassettes, flash memory cards, cartridges, and the like, may also be used in the operating environment, and, further, that any such media may contain computer-executable instructions for performing novel methods of the disclosed embodiments.

An operating system 716 and any number of program modules 718 or other applications can be stored in the volatile memory 710, wherein the program modules 718 represent a wide array of computer-executable instructions corresponding to programs, applications, functions, and the like that may implement the functionality described herein in whole or in part, such as through instructions 720 on the processing device 702. The program modules 718 may also reside on the storage mechanism provided by the storage device 714. As such, all or a portion of the functionality described herein may be implemented as a computer program product stored on a transitory or non-transitory computer-usable or computer-readable storage medium, such as the storage device 714, non-volatile memory 708, volatile memory 710, instructions 720, and the like. The computer program product includes complex programming instructions, such as complex computer-readable program code, to cause the processing device 702 to carry out the steps necessary to implement the functions described herein.

An operator, such as the user, may also be able to enter one or more configuration commands to the computer system 700 through a keyboard, a pointing device such as a mouse, or a touch-sensitive surface, such as the display device, via an input device interface 722 or remotely through a web interface, terminal program, or the like via a communication interface 724. The communication interface 724 may be wired or wireless and facilitate communications with any number of devices via a communications network in a direct or indirect fashion. An output device, such as a display device, can be coupled to the system bus 706 and driven by a video port 726. Additional inputs and outputs to the computer system 700 may be provided through the system bus 706 as appropriate to implement embodiments described herein.

The operational steps described in any of the exemplary embodiments herein are described to provide examples and discussion. The operations described may be performed in numerous different sequences other than the illustrated sequences. Furthermore, operations described in a single operational step may actually be performed in a number of different steps. Additionally, one or more operational steps discussed in the exemplary embodiments may be combined.

Those skilled in the art will recognize improvements and modifications to the preferred embodiments of the present disclosure. All such improvements and modifications are considered within the scope of the concepts disclosed herein and the claims that follow.

What is claimed is:

1. A method for detecting abnormalities in video data, the method comprising:
receiving video data comprising a plurality of color channels, the plurality of color channels comprising a red color channel, a green color channel, and a blue color channel;
beamforming each of the plurality of color channels in a region of interest on skin of a subject into a color time-series to enhance vital sign information, the beamforming based on an equation:

$$[R_j^i; G_j^i; B_j^i] = \left[\frac{\sum_{ROI,k}\text{pixel}_k^{red}}{|ROI|}; \frac{\sum_{ROI,k}\text{pixel}_k^{green}}{|ROI|}; \frac{\sum_{ROI,k}\text{pixel}_k^{blue}}{|ROI|}\right],$$

where $R_j^i$ denotes a red color channel value at an i-th processing interval at a j-th index; $G_j^i$ denotes a green color channel value at the i-th processing interval at the j-th index; $B_j^i$ denotes a blue color channel value at the i-th processing interval at the j-th index; and ROI denotes a number of pixels in the region of interest;
extracting the vital sign information of the subject from the color time-series, the extracting including applying color beamforming weights to the color time-series, wherein the color beamforming weights are based on a spectral energy distribution of the color time-series within a frequency range of interest using a constructed spectral covariance matrix;
analyzing the vital sign information; and
determining whether an abnormality occurs in the analyzed vital sign information.

2. The method of claim 1, wherein the video data comprises a plurality of frames.

3. The method of claim 2, further comprising tracking movement of the region of interest across the plurality of frames.

4. The method of claim 2, further comprising spatially averaging changes in each of the plurality of color channels in the region of interest across the plurality of frames.

5. The method of claim 4, further comprising adaptively beamforming the spatially averaged changes in each of the plurality of color channels to enhance indications of a pulse of the subject.

6. The method of claim 1, further comprising applying a face recognition algorithm to the video data to determine the region of interest.

7. The method of claim 6, wherein the face recognition algorithm is a multiple-face recognition algorithm which determines additional regions of interest.

8. The method of claim 1, wherein the vital sign information comprises a heart rate of the subject and the frequency range of interest is a frequency range of the heart rate.

9. The method of claim 8, wherein analyzing the vital sign information comprises analyzing variations in the heart rate of the subject.

10. The method of claim 9, wherein determining whether the abnormality occurs in the analyzed vital sign information comprises determining whether the heart rate of the subject is abnormally constant or has an abnormal variation in beat to beat intervals.

11. The method of claim 1, wherein the vital sign information comprises a respiration rate of the subject and the frequency range of interest is a frequency range of the respiration rate.

12. A fraud detector, comprising:
a memory; and
a signal processor coupled to the memory and configured to:
obtain video data stored in the memory and comprising a plurality of color channels, the plurality of color channels comprising a red color channel, a green color channel, and a blue color channel;
beamform each of the plurality of color channels in a region of interest on skin of a subject into a color time series to enhance vital sign information, the beamforming based on an equation:

$$[R^i_j; G^i_j; B^i_j] = \left[ \frac{\sum_{ROI,k} \text{pixel}_k^{red}}{|ROI|}; \frac{\sum_{ROI,k} \text{pixel}_k^{green}}{|ROI|}; \frac{\sum_{ROI,k} \text{pixel}_k^{blue}}{|ROI|} \right],$$

where denotes a red color channel value at an i-th processing interval at a j-th index; $G_j^i$ denotes a green color channel value at the i-th processing interval at the j-th index; $B_j^i$ denotes a blue color channel value at the i-th processing interval at the j-th index; and ROI denotes a number of pixels in the region of interest;

extract the vital sign information of the subject from the color time-series, the extracting comprising applying color beamforming weights to the color time-series, wherein the color beamforming weights are based on a spectral energy distribution of the color time-series within a frequency range of interest using a constructed spectral covariance matrix;

analyze the vital sign information to detect an abnormality; and if the abnormality is detected, determine the video data is fraudulent.

13. The fraud detector of claim 12, wherein the signal processor is further configured to apply a face recognition algorithm to the video data to determine and track the region of interest over time.

14. The fraud detector of claim 13, wherein the signal processor is further configured to extract the vital sign information by:

tracking changes in each of the plurality of color channels in the region of interest over time; and adaptively beamforming the changes in each of the plurality of color channels to produce the vital sign information.

15. The fraud detector of claim 12, wherein the signal processor is further configured to analyze the vital sign information to detect the abnormality by analyzing variations in the vital sign information of the subject.

16. A method for detecting fraudulent video data, the method comprising:

receiving video data comprising a plurality of color channels, the plurality of color channels comprising a red color channel, a green color channel, and a blue color channel;

beamforming each color channel in the plurality of color channels in a region of interest on skin of a subject into a color time-series to enhance vital sign information, the beamforming based on an equation:

$$[R^i_j; G^i_j; B^i_j] = \left[ \frac{\sum_{ROI,k} \text{pixel}_k^{red}}{|ROI|}; \frac{\sum_{ROI,k} \text{pixel}_k^{green}}{|ROI|}; \frac{\sum_{ROI,k} \text{pixel}_k^{blue}}{|ROI|} \right],$$

where $R_j^i$ denotes a red color channel value at an i-th processing interval at a j-th index; $G_j^i$ denotes a green color channel value at the i-th processing interval at the j-th index; $B_j^i$ denotes a blue color channel value at the i-th processing interval at the j-th index; and ROI denotes a number of pixels in the region of interest;

extracting the vital sign information of the subject from the color time-series, the extracting comprising applying color beamforming weights to the color time-series, wherein the color beamforming weights are based on a spectral energy distribution of the color time-series within a frequency range of interest using a constructed spectral covariance matrix;

analyzing the vital sign information to detect an abnormality; and determining the video data is fraudulent based on the abnormality.

17. The method of claim 16, wherein extracting the vital sign information of the subject comprises:

tracking changes in each of the plurality of color channels in the region of interest over time; and adaptively beamforming the changes in each of the plurality of color channels to produce the vital sign information.

18. The method of claim 17, wherein determining the video data is fraudulent is further based on background color changes.

19. The method of claim 17, wherein determining the video data is fraudulent is further based on at least one of edge detection or edge motion.

\* \* \* \* \*